United States Patent [19]

Kohl et al.

[11] Patent Number: 5,063,044

[45] Date of Patent: Nov. 5, 1991

[54] CARBOXY AND CARBOXY-GLYCOL ETHER AND ESTER FUNCTIONAL SILOXANE CONTAINING HAIR CONDITIONERS AND SHAMPOOS

[75] Inventors: Gretchen S. Kohl; Patricia A. Giwa-Agbomeirele; Judith M. Vincent, all of Midland County, Mich.

[73] Assignee: Dow Corning Corporation, Midland, Mich.

[21] Appl. No.: 481,003

[22] Filed: Feb. 16, 1990

[51] Int. Cl.$^5$ .................. A61K 7/075; A61K 7/08; A61K 7/09; A61K 7/13

[52] U.S. Cl. ........................... 424/70; 424/72; 424/71; 424/78; 252/DIG. 13; 252/174.15; 514/772; 514/938; 8/405

[58] Field of Search .............. 424/70, 78, 72, 71; 514/772, 937, 938, 941; 252/DIG. 13, 174.15; 8/405

[56] References Cited

U.S. PATENT DOCUMENTS

| | | | |
|---|---|---|---|
| 4,271,215 | 6/1981 | Coon | 427/387 |
| 4,366,001 | 12/1982 | Ona et al. | 106/287.11 |
| 4,477,514 | 10/1984 | Gee et al. | 428/264 |
| 4,501,619 | 2/1985 | Gee | 524/588 X |
| 4,559,227 | 12/1985 | Chandra et al. | 424/70 |
| 4,563,347 | 1/1986 | Starch | 424/70 |
| 4,587,320 | 5/1986 | Swihart | 528/23 |
| 4,744,978 | 5/1988 | Homan et al. | 424/70 |
| 4,857,212 | 8/1989 | Ona et al. | 252/8.6 |
| 4,866,152 | 9/1989 | Lo | 528/25 |

OTHER PUBLICATIONS

"Silicones for Conditioning Damaged Hair", Michael Starch, Soap Cosmetics Chemical Specialties, 1986.
"An Introduction to the Formulation of Shampoos", Charles Fox, Cosmetics & Toiletries, vol. 103, Mar. 1988.

*Primary Examiner*—Thurman K. Page
*Assistant Examiner*—Susan S. Rucker
*Attorney, Agent, or Firm*—Jim L. DeCesare

[57] ABSTRACT

A hair conditioning composition being a mixture including water, a thickener, and an organosilicon compound is disclosed. Also disclosed is a hair shampoo conditioning composition in the form of a mixture including water, at least one surfactant, a thickener, and an organosilicon conditioning compound. In both compositions, the organosilicon compound is a siloxane selected from the group consisting of carboxy functional polysiloxanes, carboxy-glycol ether functional polysiloxanes, and carboxy-glycol ester functional polysiloxanes. These compositions may also include dyes, neutralizing agents, or reducing agents, if desired.

7 Claims, No Drawings

CARBOXY AND CARBOXY-GLYCOL ETHER AND ESTER FUNCTIONAL SILOXANE CONTAINING HAIR CONDITIONERS AND SHAMPOOS

BACKGROUND OF THE INVENTION

This invention relates to a hair conditioning composition which is a mixture including water, a thickener, and an organosilicon compound which is a polyorganosiloxane; and to a hair shampoo conditioning composition in the form of a mixture including water, at least one surfactant, a thickener, and a conditioning compound. More particularly, the conditioning compound is a siloxane selected from the group consisting of carboxy functional polysiloxanes, carboxy-glycol ether functional polysiloxanes and carboxy-glycol ester functional polysiloxanes.

The term "conditioner" in relation to hair grooming preparations, refers to an ingredient for enhancing the manageability, appearance and feel of treated hair. Such materials should be capable of acting as a lubricant, reduce the resistance of wet or dry hair to combing, minimize tangling, make hair softer and smoother, improve its set retention when styled, and act as an antistatic agent, reducing or eliminating the phenomenon of 'flyaway' due to the accumulation of static electricity without producing build-up on repeated application which in turn causes hair to become lank and dull. Another function of hair conditioners is to improve curl retention and to impart body and gloss to hair. Materials which are substantive to hair are more effective in this respect. Quaternary ammonium compounds, like cetyl trimethyl ammonium chloride, have been shown to be effective as conditioners at concentrations as low as 0.5%. Silicones can be used at even lower concentrations.

Hair conditioning is a surface treatment aimed at improving the condition of the hair in terms of the attributes just mentioned. It only affects the hair shaft outermost layer or the cuticle. The latter, apart from having a protective function for the layers below it, also determines the frictional properties of hair and hence its feel. It has been found that hair conditioners containing a quaternary compound or a silicone are effective in reducing damage to hair during combing and brushing by reducing friction between comb, brush and hair. This effect is improved when the lubricant is substantive to hair.

The phenomenon of "flyaway" has been corrected by the neutralization of the static charges generated by combing with a conditioning agent that lubricates the fibers. The parallel alignment of hair fibers by a material with the correct refractive index has also led to improvements in hair gloss. "Hair body" as a conditioning aspect is assessed by a subjective evaluation of the user as to the appearance and general feel of the treated hair. An increase in interfiber static friction imparts body by creating bridges between fibers. It should therefore be apparent that the conditioning function is an important aspect in hair care applications in addition to the more general requirement relating to cleanliness. Silicones are capable of providing the many conditioning benefits noted above, and offer an alternative conditioning agent to conventional organic equivalents. In certain instances, combinations of organic conditioning agents and silicone conditioning agents have been found to be advantageous.

Aminofunctional siloxanes are known in the hair care and fabric care industries as conditioners and softeners, respectively. The aminofunctional materials are applied to hair in the form of a conditioning shampoo, pre-rinse or post-rinse conditioner. Aminofunctional siloxanes are also commonly added to hair dyes and permanent wave systems for their conditioning effect. In fabric care applications, aminofunctional siloxanes are applied to fabric in the form of a fabric softener component of a laundry detergent, or as an ingredient in a rinse cycle softener. Aminofunctional siloxanes may also be applied to fabrics in a dryer by means of a dryer sheet impregnated with the softening composition.

In addition to conditioning hair and softening fabrics, another characteristic of aminofunctional siloxanes is their substantivity to hair and fabrics to which they are applied. Hair and fabrics treated with aminofunctional siloxanes are known to retain their conditioned or softened qualities through several washings.

Such aminofunctional siloxanes are shown, for example, U.S. Pat. No. 4,559,227, issued Dec. 17, 1985; and in U.S. Pat. No. 4,563,347, issued Jan. 7, 1986. The siloxanes in the '227 and '347 patents are employed as constituents in hair shampoo and hair conditioning formulations, respectively. In U.S. Pat. No. 4,866,152, issued Sept. 12, 1989, such siloxanes are employed in fabric treatment operations. While these siloxanes are known to provide acceptable levels of performance in hair and fabric treatment applications, the aminofunctional siloxanes have some disadvantages. For example, aminofunctional siloxane compounds tend to irritate the skin upon repeated exposure, and have a yellowing tendency upon application to lighter colored hair and fabric. Such siloxanes have also been known to generate an unpleasant odor which consumers find less than desirable in certain applications.

In contrast to the above, the carboxy, carboxy-glycol ether, and carboxy-glycol ester, functional polysiloxanes of the present invention suffer from none of the foregoing disadvantages of the aminofunctional siloxanes noted, and provide performance characteristics equivalent to, if not better than, the aminofunctional materials. For example, it has been shown that a single semi-occluded skin contact for twenty-four hours results in no detectable irritation. It has also been shown that lighter colored hair treated with the Materials of the present invention possess less tendency to yellow. However, neither carboxy nor carboxy-glycol ester siloxanes are new. Carboxy functional siloxanes, for example, are disclosed in U.S. Pat. No. 4,271,215, issued June 2, 1981; U.S. Pat. No. 4,477,514, issued Oct. 16, 1984; U.S. Pat. No.. 4,744,978, issued May 17, 1988; and in U.S. Pat. No. 4,857,212, issued Aug. 15, 1989. Carboxy-glycol ester functional siloxanes on the other hand are taught, for example, in U.S. Pat. No. 4,366,001, issued Dec. 28, 1982; and in U.S. Pat. No. 4,587,320, issued May 6, 1986. However, none of the foregoing patents are specific to hair conditioning applications of the carboxy and carboxy-glycol ester functional polysiloxanes, nor do they teach one skilled in the art how to produce specific conditioning formulations for successfully applying such siloxanes to the hair.

SUMMARY OF THE INVENTION

This invention is directed to a hair conditioning composition in the form of a mixture including water, a thickener, and an organosilicon compound which is a polyorganosiloxane. The siloxane is selected from the group consisting of carboxy functional polysiloxanes, carboxy-glycol ether functional polysiloxanes, and carboxy-glycol ester functional polysiloxanes. In the case of the carboxy functional polysiloxane compound, the compound may be present in the mixture in the form of an emulsion or microemulsion of the polysiloxane in water.

The invention is also directed to a hair shampoo conditioning composition which is a mixture including water, at least one surfactant, a thickener, and a conditioning compound. As in the case of the hair conditioning composition described above, the conditioning compound employed in the shampoo is a siloxane selected from the group consisting of carboxy functional polysiloxanes, carboxy-glycol ether functional polysiloxanes, and carboxy-glycol ester functional polysiloxanes. The carboxy functional polysiloxane compound may also be present in the mixture in the form of an emulsion or microemulsion of the polysiloxane in water. The surfactant can be an anionic surfactant, and the mixture may also include a second surfactant in addition to the anionic surfactant. The second surfactant can be an amphoteric surfactant.

These and other features, objects, and advantages, of the herein described present invention will be more clearly understood from a consideration of the following detailed description thereof.

DETAILED DESCRIPTION OF THE INVENTION

In accordance with the present invention, there is provided a hair conditioning composition which is a mixture including water, a thickener, and an organosilicon compound. A hair shampoo conditioning composition is also disclosed herein and relates to a mixture including water, at least one surfactant, a thickener, and an organosilicon conditioning compound. The organosilicon compound used in either the conditioner formulation or the shampoo formulation is a siloxane selected from the group consisting of carboxy functional polysiloxanes, carboxy-glycol ether functional polysiloxanes, and carboxy-glycol ester functional polysiloxanes. The polysiloxanes of the present invention have a formula selected from the group consisting of

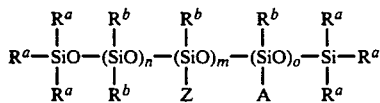  (I)

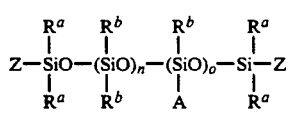  (II)

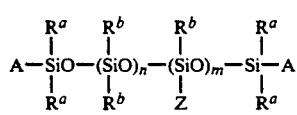  (III)

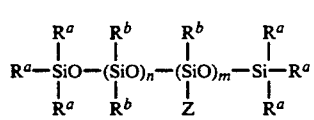  (IV)

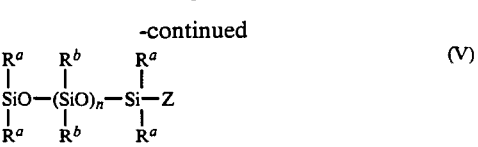  (V)

wherein
$R^a$ is selected from the group consisting of hydrogen, alkyl and alkoxy radicals having one to eighteen carbon atoms, Z, or A;
$R^b$ is selected from the group consisting of hydrogen, alkyl and alkoxy radicals having one to three carbon atoms, Z, or A;
Z is represented by the group $-R^cX$;
$R^c$ is selected from the group consisting of divalent alkyl radicals having one to eighteen carbon atoms or $-R^dSiOSiOR^d-$;
$R^d$ is selected from the group consisting of divalent alkyl and ether radicals having two to four carbon atoms;
X is a carboxy group selected from the group consisting of $-R^bOOR^e$ or $-SCH_2R^bOOR^e$;
$R^e$ is selected from the group consisting of hydrogen or alkyl radicals having one to four carbon atoms;
n, m, and o, are each integers of from one to about five thousand; and
A represents a glycol ether group having the formula $-(CH_2)_3-O(CH_2CH_2O)_y-R^e$ in which y is an integer of from one to about one hundred, or A represents a glycol ester group having the formula $-(CH_2)_3-O(CH_2CH_2O)_y-COR^e$ in which y is an integer of from one to about one hundred. The preferred glycol ether group has the formula $-(CH_2)_3-O(CH_2CH_2O)_y-CH_3$ whereas the preferred glycol ester group has the formula $-(CH_2)_3-O(CH_2CH_2O)_y-COOH_3$.

Formulas I, II, and III, set forth above are each directed to carboxy-glycol ether or ester functional siloxanes, while Formulas IV and V relate to carboxy functional siloxanes, in accordance with the present invention.

In the above formulas, the integers n, m, and o, each preferably can have a value of one to about one thousand, however, in the most preferred embodiment of the present invention, the integers n, m, and o, are each from one to about five hundred. The integer y can more preferably have a value of from thirty to about sixty. Representative of compounds preferred in accordance with the present invention are a carboxy-glycol ether functional polysiloxane compound having the formula

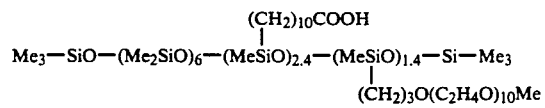

and a carboxy functional polysiloxane compound having the formula

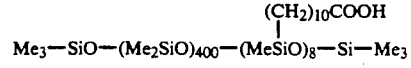

wherein Me is methyl.

The carboxy functional polysiloxane compound may be present in the mixture in the form of an emulsion or microemulsion of the polysiloxane in water. The hair shampoo conditioning composition includes a surfactant, and the surfactant may be an anionic surfactant. The shampoo mixture also may include a second surfactant in addition to the anionic surfactant, and the second surfactant can constitute an amphoteric surfactant, although other surfactant combinations may be employed within the concept of the present invention.

The $C_1$–$C_{18}$ alkyls represented by $R^a$ include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl and octadecyl. The $C_1$–$C_{18}$ alkoxys represented by $R^a$ include methoxy, ethoxy, propoxy, butoxy, pentoxy, hexoxy, heptoxy, octoxy, nonoxy, decoxy, undecoxy, dodecoxy, tridecoxy, tetradecoxy, pentadecoxy, hexadecoxy, heptadecoxy and octadecoxy. The $C_1$–$C_3$ alkyls represented by $R^b$ include methyl, ethyl and propyl. The $C_1$–$C_3$ alkoxys represented by $R^b$ include methoxy, ethoxy and propoxy. The $C_1$–$C_{18}$ divalent alkyls represented by $R^c$ include methylene, ethylene, propylene, butylene, pentylene, hexylene, heptylene, octylene, nonylene, decylene, undecylene, dodecylene, tridecylene, tetradecylene, pentadecylene, hexadecylene, heptadecylene and octadecylene. The $C_2$–$C_4$ divalent alkyls represented by $R^d$ include ethylene, propylene and butylene. The $C_2$–$C_4$ divalent ethers represented by $R^d$ include ethylene ether, propylene ether and butylene ether. The $C_1$–$C_4$ alkyls represented by $R^e$ include methyl, ethyl, propyl, and butyl.

The shampoo compositions of this invention contain a surfactant selected from the group consisting of anionic and amphoteric surfactants. The surfactant functions as a foaming and cleansing agent in the shampoo composition. The identity of the surfactant in the shampoo compositions of this invention is not critical as long as the surfactant system in the shampoo is capable of cleaning the hair and providing an acceptable level of foam on the hair. The surfactant system may comprise one or more water soluble detergents, i.e., an anionic or amphoteric surfactant which produces an acceptable level of foam and cleaning for the hair.

Anionic detergents are preferred since they provide richer, denser foams than other types of detergents at comparable concentrations. It is desirable for that reason that the surfactant system contain at least one anionic detergent. Suitable anionic detergents include sulfonated and sulfated alkyl, aralkyl and alkaryl anionic detergents; alkyl succinates; alkyl sulfosuccinates and N-alkoyl sarcosinates. Especially preferred are the sodium, magnesium, ammonium, and the mono-, di- and triethanolamine salts of alkyl and aralkyl sulfates as well as the salts of alkaryl sulfonates. The alkyl groups of the detergents generally have a total of from about 12 to 21 carbon atoms, may be unsaturated, and are preferably fatty alkyl groups. The sulfates may be sulfate ethers containing one to ten ethylene oxide or propylene oxide units per molecule. Preferably, the sulfate ethers contain 2 to 3 ethylene oxide units.

Typical anionic detergents include, among others, sodium lauryl sulfate, sodium lauryl ether sulfate, ammonium lauryl sulfate, triethanolamine lauryl sulfate, sodium C14–16 olefin sulfonate, ammonium pareth-25 sulfate (ammonium salt of a sulfated polyethylene glycol ether of a mixture of synthetic C12–15 fatty alcohols), sodium myristyl ether sulfate, ammonium lauryl ether sulfate, disodium monooleamidosulfosuccinate, ammonium lauryl sulfosuccinate, sodium dodecylbenzene sulfonate, triethanolamine dodecylbenzene sulfonate and sodium N-lauroyl sarcosinate. The most preferred anionic detergents are the lauryl sulfates, particularly monoethanolamine, triethanolamine, ammonium and sodium lauryl sulfates. Sodium lauryl ether sulfate is also very suitable for use in the compositions of this invention.

Surfactants generally classified as amphoteric or ampholytic detergents include, among others, cocoamphocarboxyglycinate, cocoamphocarboxypropionate, cocobetaine, N-cocamidopropyldimethylglycine, and N-lauryl-N'-carboxymethyl-N'-(2-hydroxyethyl)ethylenediamine. Other suitable amphoteric detergents include the quaternary cycloimidates, betaines, and sultaines disclosed in U.S. Pat. No. 3,964,500. Particularly preferred amphoteric surfactants are the substituted quaternary hydroxy cycloimidinic acid alkali metal alcoholates described in U.S. Pat. No. 2,528,378.

The most preferred of the amphoteric surfactants are the substituted quaternary hydroxy cycloimidinic acid alkali metal alkoxymethyl carboxylates described in U.S. Pat. No. 2,781,354. The betaines may have the structure:

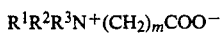

$$R^1R^2R^3N^+(CH_2)_mCOO^-$$

wherein $R^1$ is an alkyl group having about 12 to 18 carbon atoms or a mixture thereof, $R^2$ and $R^3$ are independently lower alkyl groups having 1 to 3 carbon atoms, and m is an integer from 1 to 4. Specific betaines useful in the products of the invention are for example alpha-(tetradecyldimethylammonio)acetate, beta-(hexadecyldiethylammonio)propionate, and gamma-(dodecyldimethylammonio)butyrate.

The sultaines may have the structure:

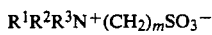

$$R^1R^2R^3N^+(CH_2)_mSO_3^-$$

wherein $R^1$, $R^2$, $R^3$, and m are defined as above. Specific useful sultaines are for example 3-(dodecyldimethylammonio)-propane-1-sulfonate, and 3-(tetradecyldimethylammonio)ethane-1-sulfonate.

The shampoo compositions of this invention may contain a nonionic surfactant. The nonionic surfactants useful in the present invention are selected from the group consisting of fatty acid alkanolamide and amine oxide surfactants. The fatty acid alkanolamides are nonionic surfactants obtained by reacting alkanolamines such as monoethanolamine, diethanolamine, monoisopropanolamine, or diisopropanolamine with a fatty acid or fatty acid ester to form the amide. The hydrophobic portion of the nonionic surfactant is provided by a fatty acid hydrocarbon chain which generally has from 10 to 21 carbon atoms. The fatty acid alkanolamide surfactants include, for example, fatty acid diethanolamides such as isostearic acid diethanolamide, lauric acid diethanolamide, capric acid diethanolamide, coconut fatty acid diethanolamide, linoleic acid diethanolamides, myristic acid diethanolamide, oleic acid diethanolamide, and stearic acid diethanolamide; fatty acid monoethanolamides such as coconut fatty acid monoethanolamide; and fatty acid monoisopropanolamides such as oleic acid monoisopropanolamide and lauric acid monoisopropanolamide.

The amine oxides are well known nonionic surfactants usually obtained by oxidizing a tertiary amine to form the amine oxide. They are sometimes also referred to as polar nonionic surfactants. Amine oxide surfactants include, for example, the N-alkyl amine oxides such as N-cocodimethylamine oxide, N-lauryl dimethylamine oxide, N-myristyl dimethylamine oxide, and N-stearyl dimethylamine oxide; the N-acyl amine oxides such as N-cocamidopropyl dimethylamine oxide and N-tallowamidopropyl dimethylamine oxide; and N-alkoxyalkyl amine oxides such as bis(2-hydroxyethyl) $C_{12-15}$ alkoxy-propylamine oxide. The hydrophobic portion of the amine oxide surfactants is generally provided by a fatty hydrocarbon chain containing from 10 to 21 carbon atoms.

For purposes of this invention the alkanolamide and amine oxide surfactants are preferred. In general, the fatty acid diethanolamides and N-alkyl dimethylamine oxides are preferred for use in the shampoo compositions. Especially preferred are the fatty acid diethanolamides and N-alkyl dimethylamine oxides where the fatty hydrocarbon chain contains from 10 to 18 carbon atoms. For example, especially preferred nonionic surfactants include lauric acid diethanolamide, N-lauryl dimethylamine oxide, coconut acid diethanolamide, myristic acid diethanolamide, and oleic acid diethanolamide.

Other adjuvants may be added to the compositions of this invention such as thickeners, perfumes, colorants, electrolytes, pH control ingredients, antimicrobials, antioxidants, ultraviolet light absorbers and medicaments. For example, it is usually preferred to employ a thickener in the shampoo compositions to facilitate the hand application of the shampoo to the hair. Thickeners are preferably used in sufficient quantities to provide a convenient viscosity. For example, viscosities within the range of 400 to 6000 cps or more preferably in the range of 1000 to 4000 cps as measured at 25° C. are usually suitable.

Suitable thickeners, include, among others, sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose, and starch amylose, locust bean gum, electrolytes such as NaCl, saccharides such as fructose and glucose, and derivatives of saccharides such as PEG-120 methyl glucose dioleate. Preferred thickeners include the cellulose derivatives and saccharide derivatives. The glucose derivative, PEG-120 methyl glucose dioleate, is especially preferred in the the shampoos of the present invention.

The perfumes which can be used in the shampoo compositions are the cosmetically acceptable perfumes. Colorants are used to confer a color to the shampoo and may generally be used. Although not required, it is preferred to employ an acid to adjust the pH within the range of 5 to 9 or more preferably within the range of 6 to 8 in the shampoo compositions of this invention. Any water soluble acid such as a carboxylic acid or a mineral acid is suitable. For example, suitable acids include mineral acids such as hydrochloric, sulfuric, and phosphoric, monocarboxylic acids such as acetic acid, lactic acid, or propionic acid; and polycarboxylic acids such as succinic acid, adipic acid and citric acid.

If for special purposes additional conditioners are desired, they may be added. For example, any of the well-known organic cationic hair conditioning components that are water soluble may be added. Some cationic conditioning components that may be used in the present invention to provide additional hair grooming include quaternary nitrogen derivatives of cellulose ethers, homopolymers of dimethyldiallyl-ammonium chloride, copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl)-piperazine or of piperazine-bis-acrylamide and piperazine, poly-(dimethylbutenylammonium chloride)-$\alpha,\omega$-bis-(triethanolammonium) chloride, and copolymers of vinylpyrrolidone and acrylic acid esters with quaternary nitrogen functionality. The above cationic organic polymers and others are described in more detail in U.S. Pat. No. 4,240,450 which is hereby incorporated by reference to further describe the cationic organic polymers.

Conditioning with the compositions of the present invention may be carried out in several ways. The composition may be used in the manner of "leave-in" conditioners in that the composition may be applied to hair subsequent to washing and final rinsing. The composition may also be used in the manner of a "rinse-out" conditioner in that hair may be treated with the composition subsequent to washing but prior to final rinsing. The composition has sufficient substantivity so that its conditioning properties are retained even after the hair has been rinsed. The composition may also be used to treat hair in the fashion of shampoo containing a conditioner. In this instance, the shampoo would contain a predetermined quantity of the conditioning composition which would contact the hair at the time of washing. Hair treated with the siloxanes of the present invention are conditioned due to the deposition of the siloxane polymer thereon. Such conditioning is evidenced by increased ease of combing and softer feel or "hand" of hair treated therewith. Other benefits derived from the use of the hair conditioners of the present invention include an increase in the degree of hydrophobicity of treated hair. Hair treated with these polymers require shorter drying times.

Polymers of the present invention are in the fluid state at room temperature. Because they are fluids at room temperature, the polymers may be incorporated in hair care formulations neat, that is, without solvents or diluents. The polymers of the invention may be incorporated into hair products by simply mixing the polymer into a compatible solution of the product formulation or incorporating the polymer as a component of an emulsion or microemulsion in the product formulation. Formulations of shampoos, conditioners, permanent wave systems, and dyes, for example, comprise from 0.05 to 10 weight percent of the polymer of the invention based on the weight of the entire formulation. However, formulations comprising from 0.25 to 3.0 weight percent of the polymer of the invention based on the entire formulation are preferred.

The hair shampoo conditioning composition of the present invention should contain from about five to about twenty-five weight percent of at least one main cleaning surfactant such as an anionic surfactant. A second or co-surfactant can be employed, and when used the second surfactant is present in an amount of from about two to about ten percent. The thickener constitutes up to about two percent by weight of the shampoo formulation, and about 0.1 percent of a pH adjuster is generally required. As previously noted, the silicone conditioning agent of the present invention is included in amounts of up to about five percent by weight. The balance of the formulation is water, together with other optional ingredients such as perfumes, coloring agents and dyes, and preservatives. The co-surfactant performs a foam boosting function when it is used and assists in solubilizing the materials, and generally improves the performance of the main cleaning surfactant. The presence in the shampoo formulation of the second surfactant aids the cleaning ability of the shampoo and increases the aesthetics of the shampoo for the user. The carboxy, carboxy-glycol ether siloxane, and carboxy-glycol ester siloxane conditioning agents of the present invention may be present in amounts as low as 0.05-0.1 percent by weight. The hair conditioning compositions in accordance with this invention include essentially the same ingredients as the shampoo formulation except for the surfactants. In the case of the hair conditioner especially, a preservative may be required and representative preservatives which may be employed include about 0.1-0.2 weight percent of compounds such as formaldehyde, dimethyloldimethylhydantoin, 5-bromo-5-nitro-1,3-dioxane, methyl- and propyl para-hydroxybenzoates, and mixtures of such benzoates with sodium dehydroacetate, sorbic acid, and imidazolidinyl urea.

The invention is further illustrated by reference to the following examples. In the examples and in the accompanying tables, the three siloxanes evaluated are referred to as the carboxy functional siloxane which is equivalent to the compound

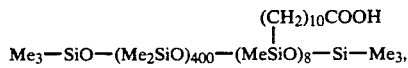

and the carboxy-glycol ether functional siloxane which is equivalent to the compound

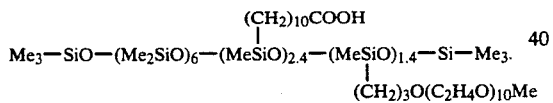

The third siloxane evaluated is an emulsion in water containing thirty percent by weight of the carboxy functional siloxane noted above. The three siloxanes were evaluated as conditioners and in shampoos, and the formulations were compared to an aminofunctional siloxane having the formula

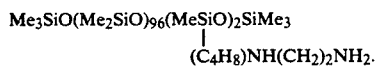

This aminofunctional siloxane was employed as an emulsion containing thirty-five percent by weight of the siloxane. Various other materials are set forth in the examples and in the tables, and by way of explanation, it is noted that the thickener referred to as NATROSOL 25OHHR is a form of hydroxyethylcellulose. COSMOCIL CQ is a conventional preservative in the form of a twenty percent mixture in water. Lauramide DEA is an alkamide of the formula

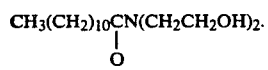

TEGO Betaine L-7 is a cocamidopropyl betaine and a zwitterion conforming generally to the formula

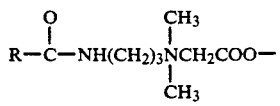

Two commercial shampoos were also evaluated. PERT PLUS ® is a shampoo containing water, ammonium lauryl sulfate, dimethicone, glycol distearate, a fragrance, ammonium xylenesulfonate, cocamide MEA, tricetylammonium chloride, xanthan gum, cetyl alcohol, sodium chloride, sodium hydroxide, methylchloroisothiazolinone, methylisothiazolinone, and various coloring agents. PRELL ® is also a commercial shampoo and contains water, TEA lauryl sulfate, SD alcohol, cocamide MEA, a fragrance, triethanolamine, hydroxypropylmethylcellulose, sodium sulfite, tetrasodium EDTA, benzophenone-2, and coloring agents.

EXAMPLE I

Preparation of Conditioner

| Standard Formulation A | |
|---|---|
| Distilled Water | 980 grams |
| Natrosol 250 HHR | 10 |
| Cosmocil C.Q. (20% in H2O) | 10 |
| Silicone Containing Conditioner | |
| Standard Formulation A | 98% |
| Silicone Polymer | 2 |
| Citric Acid (15%) | pH 5.5-6 |

In a 2000 ml beaker, the distilled water was heated to 50 degrees Centigrade on a hot plate. 10 grams of Natrosol 250 HHR was added slowly with stirring for about 15 minutes. Cosmocil C.Q. (20% in H2O) was added slowly with stirring for 5 minutes. A sample of this solution was mixed with the silicone fluid to obtain 2% silicone solids. The pH was adjusted to 5.5-6 with citric acid.

EXAMPLE II

| Anionic/Amphoteric Shampoo Formulation | |
|---|---|
| | % |
| Sodium Lauryl Ether Sulfate (25% Active) | 18.2 |
| Distilled Water | 12.5 |
| Tego Betaine L-7 | 18.2 |
| Lauramide DEA | 4.2 |
| Silicone Polymer | 2.1 |
| Distilled Water | 44.8 |

The sulfate and water were mixed in a 250 ml beaker. In a separate container, Tego Betaine L-7, Lauramide DEA and silicone polymer were mixed. Both containers were heated to 80 degrees Centigrade in a water bath. The mixture containing the silicone polymer was slowly added to the surfactant and water solution with stirring. The solution was cooled to 40 degrees Centigrade and the remaining distilled water was added. The pH was adjusted to 5.5-6.0 with 25% citric acid.

EXAMPLE III

Untreated human hair was used. A master hank of hair was subdivided into a series of individual tresses, each weight 2.0 grams. The top part of the hair was trimmed and glued to a 2"×2" plastic tab. Rubber cement was used to glue the hair to the tab. The cement was allowed to dry for one hour before the hair was combed and trimmed to six inches.

EXAMPLE IV

Treatment of Tresses for Combing with Conditioner

Each dry tress was rinsed for 30 seconds under 40 degrees Centigrade water. The tress was shampooed with three ml of 50% PRELL ® for 60 seconds and rinsed for 60 seconds using tap water at 40 degrees centigrade. The tress was hand combed and evaluated using the Instron "wet" combing method. After Instron combing, the tress was dipped in distilled water three times, and the excess water removed using two fingers. The hair was treated with one ml of test conditioner for 30 seconds and rinsed for 30 seconds under 40 degrees Centigrade tap water followed by hand combing and Instron combing.

EXAMPLE V

Treatment of Tresses for Combing with Shampoo

Each dry tress was soaked 12–30 minutes in distilled water, hand combed, and Instron-combed three times. The wet hair was treated with 0.5 ml of test shampoo. The shampoo was applied and lathered for 30 seconds, and was rinsed for 30 seconds under 40 degrees Centigrade tap water. This treatment was repeated. The hair was hand-combed and Instron-combed. After each Instron combing, the tress was dipped in distilled water three times and the excess water removed using two fingers.

Instron combing is an industry-recognized test for hair conditioner, using an Instron strain gauge equipped to measure the force required to comb hair. Each tress was evaluated using the Instron "wet" combing method. This method involves soaking the tress, if dry, for 12–30 minutes in distilled water. The hair was removed and the excess water squeezed out using two fingers. The tress was hand-combed to detangle the hair. This was followed by slowly dipping the tress into distilled water, three times, to retangle the hair. The excess water was removed using two fingers and the tress was Instron combed. The tress was Instron-combed three times following the retangling step for untreated hair and four times with treated hair.

Using the procedures as outlined above in Examples I–V, several different materials were evaluated as conditioners on hair. Table I shows the results of tests conducted using PRELL ®, a non-silicone containing formulation; a conditioner corresponding to the standard formulation A of Example I which contained no silicone; the three formulations corresponding to the compositions of the present invention containing a two percent concentration of the carboxy and carboxy-glycol ether functional siloxanes; and a formulation containing an aminofunctional siloxane. The performance of the conditioner was based on the ability of the conditioner to reduce the force used in combing the hair. Generally, the lower the percent change in the average combing load (ACL), the better is the conditioning effect. Table II shows the results of tests conducted using PRELL ®, a non-silicone containing formulation; a conditioner corresponding to the standard formulation A of Example I which contained no silicone; the formulation corresponding to only one of the compositions of the present invention containing both a one percent level and a level of 0.5 percent of the emulsion form of the carboxy functional polysiloxane; and a formulation containing an aminofunctional siloxane. Shampoo data is shown in Table III which indicates that a silicone containing shampoo, PERT PLUS, was evaluated along with formulations containing compositions equivalent to the other types indicated in Table I.

TABLE I

Instron Combing Data For Conditioners

| Treatment | Tress # | Untreated ACL | Treated ACL | % Change ACL |
|---|---|---|---|---|
| 50% (aq) Prell ® (no silicone) | 17 | 56 | 99 | 148 |
| | 47 | 36 | 145 | |
| | 62 | 54 | 88 | |
| Conditioner (no silicone) | 11 | 114 | 113 | 14 |
| | 65 | 125 | 117 | |
| | 61 | 123 | 186 | |
| Carboxy-Glycol Silicone | 8 | 114 | 110 | 32 |
| | 16 | 65 | 102 | |
| | 46 | 120 | 170 | |
| Aminofunctional Silicone | 50 | 250 | 21 | −85 |
| | 66 | 97 | 19 | |
| | 9 | 122 | 22 | |
| Carboxy Silicone Emulsion | 25 | 102 | 20 | −84 |
| | 15 | 153 | 24 | |
| | 30 | 188 | 20 | |
| Carboxy Silicone | 63 | 149 | 24 | −84 |
| | 58 | 130 | 25 | |
| | 60 | 241 | 28 | |

TABLE II

Instron Combing Data for Conditioners

| Treatment | Tress # | Untreated ACL | Treated ACL | % Change ACL |
|---|---|---|---|---|
| 50% (aq) PRELL ® (no silicone) | 53 | 292 | 835 | 182 |
| | 50 | 237 | 744 | |
| | 66 | 332 | 812 | |
| Conditioner (no silicone) | 59 | 881 | 888 | 22 |
| | 51 | 683 | 963 | |
| | 55 | 836 | 1041 | |
| 1% Aminofunctional Silicone | 73 | 930 | 186 | −86 |
| | 87 | 960 | 136 | |
| | 91 | 953 | 133 | |
| 1% Carboxy Emulsion | 88 | 870 | 57 | −92 |
| | 74 | 855 | 80 | |
| | 82 | 873 | 62 | |
| 0.5% Aminofunctional Silicone | 88 | 852 | 411 | −52 |
| | 74 | 839 | 365 | |
| | 82 | 821 | 323 | |
| 0.5% Carboxy Emulsion | 69 | 446 | 47 | −91 |
| | 52 | 620 | 38 | |
| | 60 | 553 | 53 | |

TABLE III

Instron Combing Data for Conditioning Shampoos

| Treatment | Tress # | Untreated ACL | Treated ACL | % Change ACL |
|---|---|---|---|---|
| Pert Plus ® (3% Silicone) | 40 | 46 | 32 | 43 |
| | 43 | 36 | 79 | |
| | 41 | 41 | 57 | |
| Shampoo Base (no silicone) | 12 | 45 | 63 | 77 |
| | 10 | 40 | 79 | |
| | 18 | 43 | 63 | |
| Carboxy Emulsion | 53 | 47 | 95 | 86 |
| | 13 | 46 | 77 | |
| | 1 | 52 | 98 | |
| Carboxy-Glycol Silicone | 39 | 57 | 91 | 116 |
| | 24 | 38 | 75 | |
| | 48 | 36 | 106 | |
| Carboxy Silicone | 57 | 51 | 162 | 123 |
| | 28 | 43 | 77 | |
| | 33 | 42 | 186 | |
| Aminofunctional Silicone | 34 | 33 | 133 | 267 |
| | 49 | 32 | 137 | |

TABLE III-continued

Instron Combing Data for Conditioning Shampoos

| Treatment | Tress # | Untreated ACL | Treated ACL | % Change ACL |
|---|---|---|---|---|
| | 2 | 41 | 111 | |

The compositions of the present invention may also be formulated to include dyes, colorants, reducing agents, neutralizing agents, and preservatives, necessary for their application as permanent wave systems or hair dyes, for example. The active conditioner formulation can be applied in several different forms including lotions, gels, mousses, aerosols, and pump sprays, for example, and as noted hereinbefore as conditioners and shampoos. The active conditioner includes a carrier, and suitable carrier fluids for hair care formulations are water which has already been noted, as well as, for example, such fluids as alcohols namely ethanol or isopropanol, hydrocarbons and halogenated hydrocarbons as mineral spirits and trichloroethane, cyclic siloxanes, and aerosol propellants. In those instances where it is desired to incorporate the active conditioner in the form of either an emulsion or microemulsion, such emulsions may be prepared in accordance with either U.S. Pat. No. 4,501,619, issued Feb. 26, 1985, which is directed to emulsions, or U.S. Pat. No. 4,620,878, issued Nov. 4, 1986, relating to microemulsions, each of which is incorporated herein by reference.

The compositions of the present invention should be free of any film forming resin such as cationic organic polymers sometimes employed in hair fixative compositions. For example, U.S. Pat. No. 4,744,978, issued May 17, 1988, discloses a hair fixative composition for mechanically holding the shape of the hair and including such a film forming cationic organic polymeric resin in combination with a carboxyfunctional siloxane. However, the presence of such film forming resins in the compositions of the present invention would be detrimental and would materially affect the basic and novel characteristics of the compositions of the present invention. For example, most film forming organic polymeric resins are sticky feeling or rigid to the touch, and provide hair with the feel and texture of cotton candy, which is in direct opposition to the purpose of the compositions of the present invention in providing hair with a softer and smoother feel. The compositions of the present invention may contain freeze thaw additives commonly employed in hair conditioning compositions, excluding ethylene glycol. For example, U.S. Pat. No. 4,563,347, issued Jan. 7, 1986, discloses a hair conditioning composition which includes a carboxyfunctional siloxane and an additive that provides freeze-thaw stability such as ethylene glycol and glycerol. Such freeze thaw additives have been suspected of being teratogens which are compounds believed to cause gene mutation and therefore hazards to the unborn. Such additives are therefore not desirable in the compositions of the present invention.

The carboxy functional, carboxy-glycol ether functional, and the carboxy-glycol ester functional siloxane compounds of the present invention may also be conveniently represented by the following formula:

wherein
Me is a methyl radical;
R is a carboxyfunctional radical selected from the group consisting of carboxyalkyl radicals and carboxythioalkyl radicals;
R' is selected from the group consisting of glycol ether groups having the formula $-(CH_2)_3-O(CH_2CH_2O)_a-R''$ and glycol ester groups having the formula $-(CH_2)_3-O(CH_2CH_2O)_a-COR''$ in which a is an integer of from one to about one hundred and R" is selected from the group consisting of hydrogen and alkyl radicals having one to four carbon atoms;
Q is selected from the group consisting of R, Me, and OH; and
x is an integer from one to about five thousand;
y and z are each integers from zero to about five thousand, with the proviso that when y and z are zero Q is R.

Some examples of carboxyalkyl radicals are $-CH_2CH_2COOH$, $-CH_2CH(CH_3)COOH$, $-CH_2CH(C_2H_5)CH_2COOH$, $-CH_2CH(CH_3)CH(CH_3)CH_2COOH$, and $-(CH_2)_{10}COOH$. Similarly, some examples of carboxythioalkyl radicals are $-CH_2CH_2SCOOH$, $-CH_2CH(CH_3)SCH_2COOH$, $-CH_2CH(C_2H_5)SCH_2COOH$, $-CH_2CH_2SCH_2COOH$, and $-(CH_2)_3SCOOH$.

It will be apparent from the foregoing that many other variations and modifications may be made in the compounds, compositions, structures, and methods, described herein, without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A hair conditioning composition comprising a mixture of a carrier, a thickener, and an organosilicon conditioning compound, the organosilicon conditioning compound being a carboxy-glycol ether or ester functional polysiloxane having the formula

wherein
Me is a methyl radical;
R is a carboxyfunctional radical selected from the group consisting of carboxyalkyl radicals and carboxythioalkyl radicals;
R' is selected from the group consisting of glycol ether groups having the formula $-(CH_2)_3-O(CH_2CH_2O)_a-R''$ and glycol ester groups having the formula $(CH_2)_3-O(CH_2CH_2O)_a-COR''$ in which a is an integer of from one to about one hundred and R" is selected from the group consisting of hydrogen and alkyl radicals having one to four carbon atoms;
Q is selected from the group consisting of R, Me, and OH; and
x, y and z are each integers from one to above five thousand.

2. The composition of claim 1 in which the carrier is water and wherein there is included at least one adjuvant selected from the group consisting of a dye, a reducing agent and a neutralizing agent.

3. The composition of claim 1 in which the carboxy-glycol ether or ester functional polysiloxane is present in the mixture in the form of an emulsion or microemulsion of the polysiloxane in water.

4. A hair conditioning shampoo composition comprising a mixture of a carrier, at least one surfactant, a thickener and an organosilicon conditioning compound, the organosilicon conditioning compound being a carboxy-glycol ether or ester functional polysiloxane having the formula $$QMe_2SiO(Me_2SiO)_x(MeRSiO)_y(MeR'SiO)_zSiMe_2Q$$

wherein

Me is a methyl radical;

R is a carboxyfunctional radical selected from the group consisting of carboxyalkyl radicals and carboxythioalkyl radicals;

R' is selected from the group consisting of glycol ether groups having the formula $-(CH_2)_3-O(CH_2CH_2O)_a-R''$ and glycol ester groups having the formula $-(CH_2)_3-O(CH_2CH_2O)_a-COR''$ in which a is an integer of from one to about one hundred and R'' is selected from the group consisting of hydrogen and alkyl radicals having one to four carbon atoms;

Q is selected from the group consisting of R, Me, and OH; and x, y and z are each integers from one to above five thousand.

5. The composition of claim 4 in which the carboxy-glycol ether or ester functional polysiloxane is present in the mixture in the form of an emulsion or microemulsion of the polysiloxane in water.

6. The composition of claim 4 in which the surfactant is an anionic surfactant and in which the mixture includes an amphoteric surfactant in addition to the anionic surfactant.

7. The composition of claim 4 in which the carrier is water and wherein there is included at least one adjuvant selected from the group consisting of dyes, reducing agents and neutralizing agents.

* * * * *